(12) United States Patent
Mott

(10) Patent No.: US 6,350,196 B1
(45) Date of Patent: Feb. 26, 2002

(54) DISINFECTANT DISTRIBUTION SYSTEM FOR HEATING AND COOLING DUCTS

(76) Inventor: Bruce A. Mott, 14710 Long Oak Dr., Houston, TX (US) 77070

( * ) Notice: Subject to any disclaimer, the term of this patent is extended or adjusted under 35 U.S.C. 154(b) by 0 days.

(21) Appl. No.: 09/663,125

(22) Filed: Sep. 15, 2000

(51) Int. Cl.$^7$ ................................................ B67D 5/08
(52) U.S. Cl. ..................................... 454/337; 422/124
(58) Field of Search ............................... 454/157, 328, 454/337; 422/123, 124

(56) References Cited

U.S. PATENT DOCUMENTS

| | | | |
|---|---|---|---|
| 2,664,604 A | * | 1/1954 | Hein et al. |
| 2,867,866 A | * | 1/1959 | Steele |
| 3,158,081 A | | 11/1964 | Frost |
| 3,499,579 A | | 3/1970 | Garratt |
| 3,589,563 A | | 6/1971 | Carragan |
| 3,636,862 A | * | 1/1972 | Bottas et al. |
| D271,517 S | | 11/1983 | Mori |
| 4,903,583 A | | 2/1990 | Frazier |
| 5,038,972 A | | 8/1991 | Muderlak et al. |
| 5,301,873 A | * | 4/1994 | Burke et al. ............ 454/337 X |
| 5,598,954 A | * | 2/1997 | Salzano |
| 5,755,364 A | * | 5/1998 | LeCoffre et al. |
| 5,833,929 A | * | 11/1998 | Watson et al. .......... 454/157 X |
| 5,958,346 A | * | 9/1999 | Evans, Jr. ................ 422/123 X |

* cited by examiner

Primary Examiner—Harold Joyce

(57) ABSTRACT

A disinfectant distribution system for heating and cooling ducts for purifying the air handled by a central forced-air heating or cooling system. The disinfectant distribution system for heating and cooling ducts includes a housing structure assembly including a housing having a front wall, a back wall, side walls, and a top wall, and being adapted to be securely attached to a heating and cooling duct; and also includes a conduit assembly being attached to and extended in the housing for transporting disinfectant spray from an aerosol can to the heating and cooling duct; and further includes a spray dispensing assembly being disposed in the housing and being adapted to dispense disinfectant spray from the aerosol can.

17 Claims, 3 Drawing Sheets

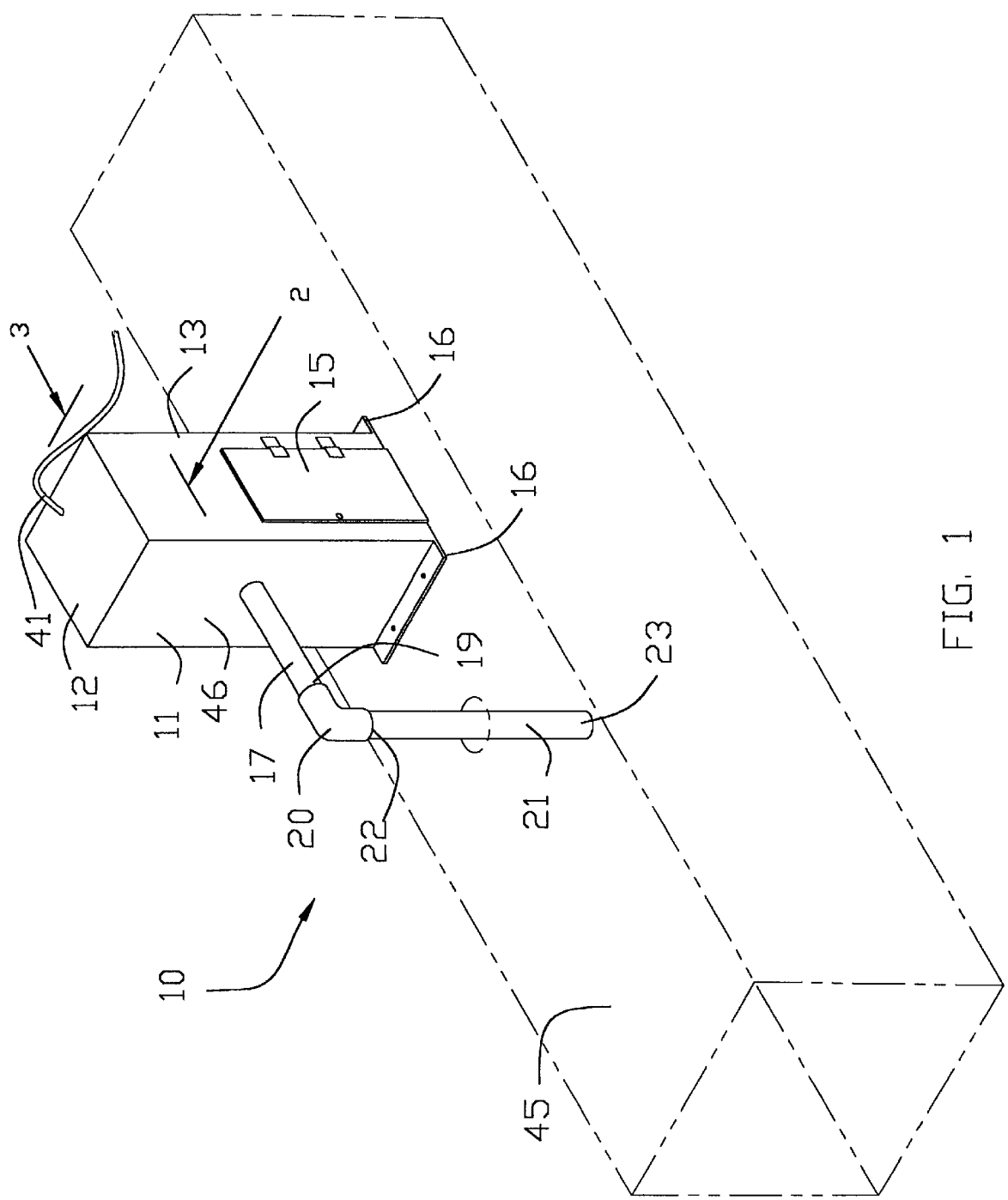

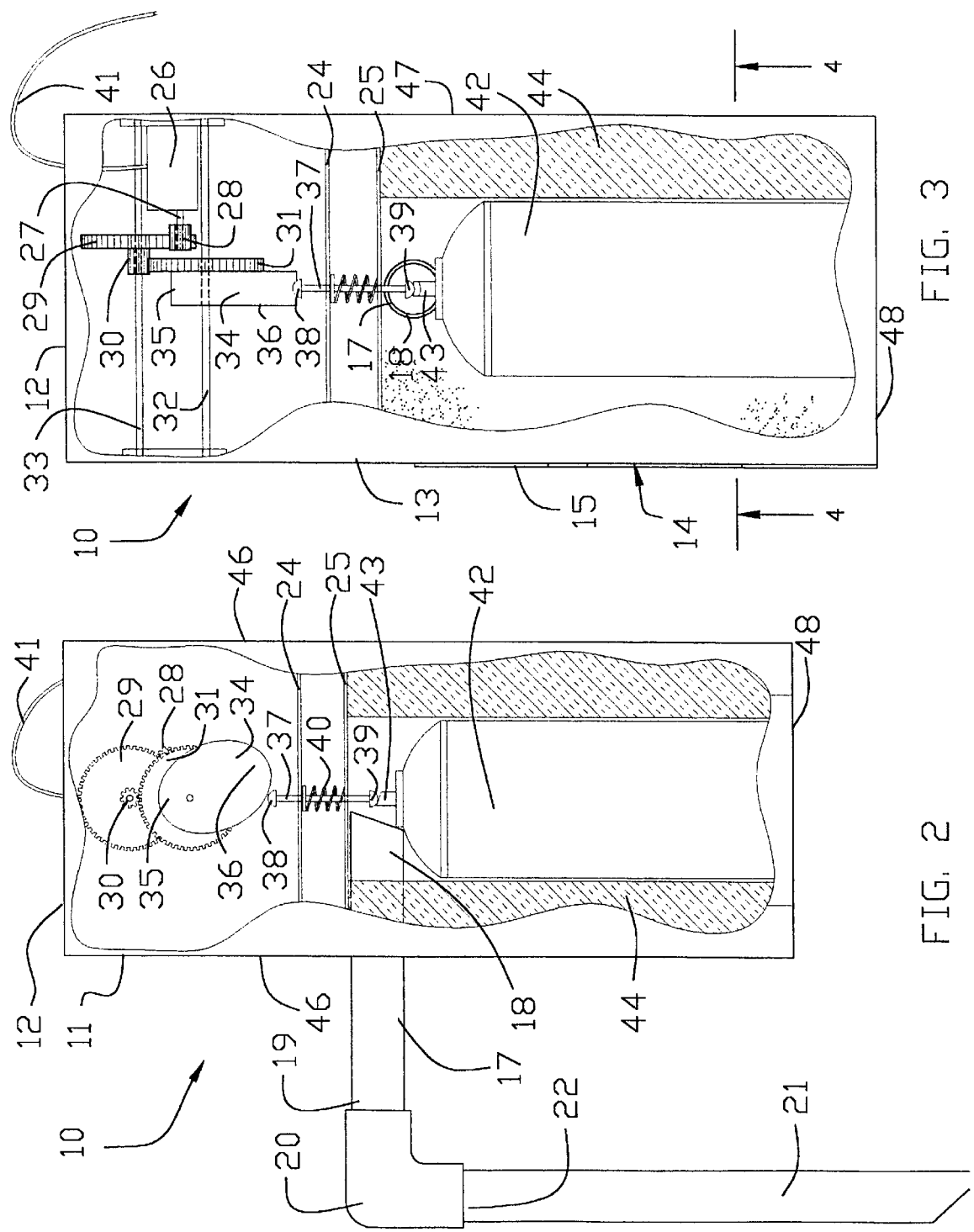

DISINFECTANT DISTRIBUTION SYSTEM FOR HEATING AND COOLING DUCTS

BACKGROUND OF THE INVENTION

1. Field of the Invention

The present invention relates to a force-air duct disinfectant system and more particularly pertains to a new disinfectant distribution system for heating and cooling ducts for purifying the air handled by a central forced-air heating or cooling system.

2. Description of the Prior Art

The use of a force-air duct disinfectant system is known in the prior art. More specifically, a force-air duct disinfectant system heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,903,583; 5,038,972; 3,589,563; 3,499,579; U.S. Pat. Des. No. 271,517; and U.S. Pat. No. 3,158,081.

While these devices fulfill their respective, particular objectives and requirements, the aforementioned patents do not disclose a new disinfectant distribution system for heating and cooling ducts. The inventive device includes a housing structure assembly including a housing having a front wall, a back wall, side walls, and a top wall, and being adapted to be securely attached to a heating and cooling duct; and also includes a conduit assembly being attached to and extended in the housing for transporting disinfectant spray from an aerosol can to the heating and cooling duct; and further includes a spray dispensing assembly being disposed in the housing and being adapted to dispense disinfectant spray from the aerosol can.

In these respects, the disinfectant distribution system for heating and cooling ducts according to the present invention substantially departs from the conventional concepts and designs of the prior art, and in so doing provides an apparatus primarily developed for the purpose of purifying the air handled by a central forced-air heating or cooling system.

SUMMARY OF THE INVENTION

In view of the foregoing disadvantages inherent in the known types of force-air duct disinfectant system now present in the prior art, the present invention provides a new disinfectant distribution system for heating and cooling ducts construction wherein the same can be utilized for purifying the air handled by a central forced-air heating or cooling system.

The general purpose of the present invention, which will be described subsequently in greater detail, is to provide a new disinfectant distribution system for heating and cooling ducts which has many of the advantages of the force-air duct disinfectant system mentioned heretofore and many novel features that result in a new disinfectant distribution system for heating and cooling ducts which is not anticipated, rendered obvious, suggested, or even implied by any of the prior art force-air duct disinfectant system, either alone or in any combination thereof.

To attain this, the present invention generally comprises a housing structure assembly including a housing having a front wall, a back wall, side walls, and a top wall, and being adapted to be securely attached to a heating and cooling duct; and also includes a conduit assembly being attached to and extended in the housing for transporting disinfectant spray from an aerosol can to the heating and cooling duct; and further includes a spray dispensing assembly being disposed in the housing and being adapted to dispense disinfectant spray from the aerosol can.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new disinfectant distribution system for heating and cooling ducts which has many of the advantages of the force-air duct disinfectant system mentioned heretofore and many novel features that result in a new disinfectant distribution system for heating and cooling ducts which is not anticipated, rendered obvious, suggested, or even implied by any of the prior art force-air duct disinfectant system, either alone or in any combination thereof.

It is another object of the present invention to provide a new disinfectant distribution system for heating and cooling ducts which may be easily and efficiently manufactured and marketed.

It is a further object of the present invention to provide a new disinfectant distribution system for heating and cooling ducts which is of a durable and reliable construction.

An even further object of the present invention is to provide a new disinfectant distribution system for heating and cooling ducts which is susceptible of a low cost of manufacture with regard to both materials and labor, and which accordingly is then susceptible of low prices of sale to the consuming public, thereby making such disinfectant distribution system for heating and cooling ducts economically available to the buying public.

Still yet another object of the present invention is to provide a new disinfectant distribution system for heating and cooling ducts which provides in the apparatuses and methods of the prior art some of the advantages thereof, while simultaneously overcoming some of the disadvantages normally associated therewith.

Still another object of the present invention is to provide a new disinfectant distribution system for heating and cooling ducts for purifying the air handled by a central forced-air heating or cooling system.

Yet another object of the present invention is to provide a new disinfectant distribution system for heating and cooling ducts which includes a housing structure assembly including a housing having a front wall, a back wall, side walls, and a top wall, and being adapted to be securely attached to a heating and cooling duct; and also includes a conduit assembly being attached to and extended in the housing for transporting disinfectant spray from an aerosol can to the heating and cooling duct; and further includes a spray dispensing assembly being disposed in the housing and being adapted to dispense disinfectant spray from the aerosol can.

Still yet another object of the present invention is to provide a new disinfectant distribution system for heating and cooling ducts that substantially improves the air quality upon the blowers for the heating and cooling ducts being turned on Even still another object of the present invention is to provide a new disinfectant distribution system for heating and cooling ducts that is easy and convenient to install and is quite effective in eliminating bacteria which causes much of the illness to people.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new disinfectant distribution system for heating and cooling ducts according to the present invention.

FIG. 2 is a front cross-sectional view of the present invention.

FIG. 3 is a side cross-sectional view of the present invention.

DESCRIPTION OF THE PREFERRED EMBODIMENT

Figure 4:
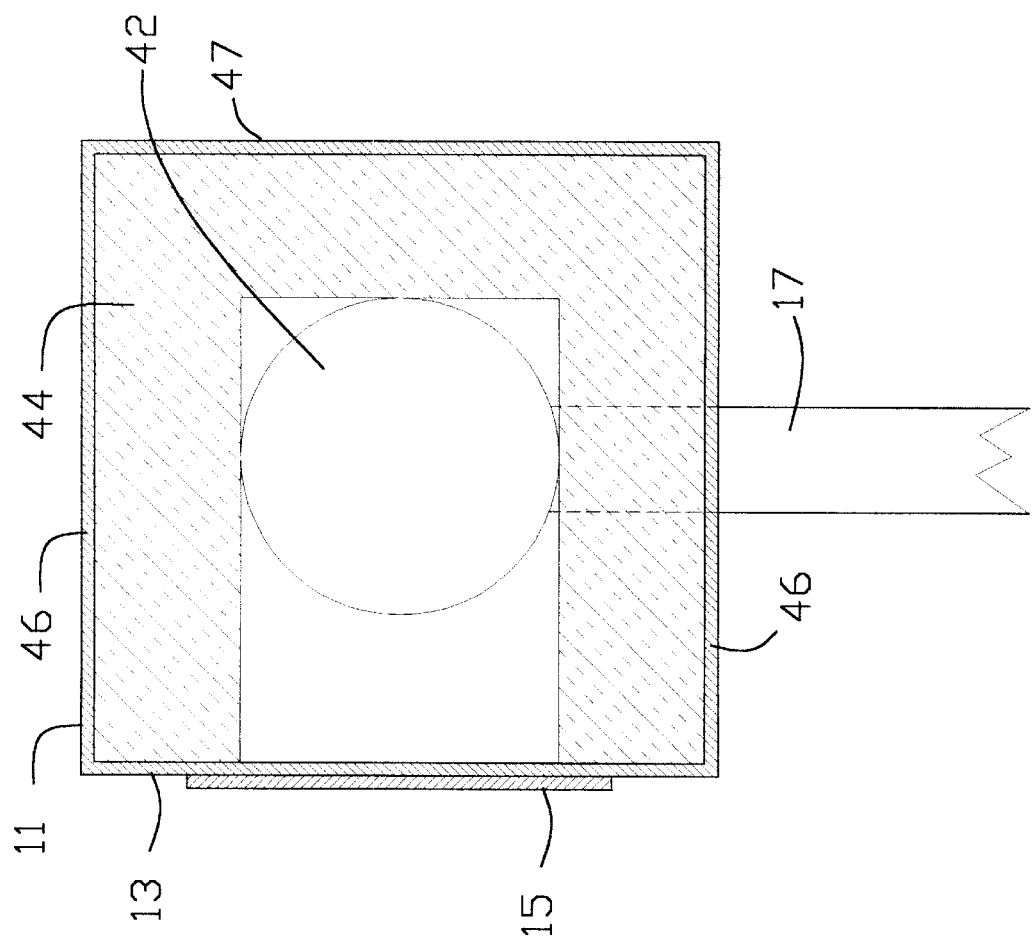
FIG. 4 is a bottom cross-sectional view of the present invention.

With reference now to the drawings, and in particular to FIGS. 1 through 4 thereof, a new disinfectant distribution system for heating and cooling ducts embodying the principles and concepts of the present invention and generally designated by the reference numeral 10 will be described.

As best illustrated in FIGS. 1 through 4, the disinfectant distribution system for heating and cooling ducts 10 generally comprises a housing structure assembly including a housing 11 having a front wall 13, a back wall 47, side walls 46, and a top wall 12, and being adapted to be securely and conventionally attached to a heating and cooling duct 45. The housing structure assembly further includes an access opening 14 disposed through the front wall 13 of the housing 11, and also includes a door 15 removably closed over the access opening 14, and further includes flange members 16 extending along bottom ends of the side walls 46 and being adapted to securely mount the housing 11 to the heating and cooling duct 45 with fasteners. The housing 11 is adapted to receive and store an aerosol can 42 therein. The housing structure also includes a first intermediate wall 24 being disposed in the housing 11 and being conventionally attached to the side walls 46 thereof, and further includes a second intermediate wall 25 being disposed below and spaced from the first intermediate wall 24 in the housing 11. The housing structure assembly also includes insulating material 44 lining the side walls 46, back wall 47, and front wall 13 in the housing 11 between the second intermediate wall 25 and the bottom wall 48 of the housing 11.

A conduit assembly is conventionally attached to and extended in the housing 11 for transporting disinfectant spray from the aerosol can 42 to the heating and cooling duct 45. The conduit assembly includes a first tubular member 17 having a first end 18 extended in the housing 11 through one of the side walls 46 thereof and being adapted to be in alignment with a nozzle 43 of the aerosol can 42, and also includes a tubular elbow member 20 being conventionally mounted to a second end 19 of the first tubular member 17, and further includes a second tubular member 21 having a first end 22 and a second end 23 which is adapted to extend in the heating and cooling duct 45 with the first end 22 of the second tubular member 21 being conventionally attached to the tubular elbow member 20.

A spray dispensing assembly is conventionally disposed in the housing 11 and is adapted to dispense disinfectant spray from the aerosol can 42. The spray dispensing assembly includes a motor 26 securely and conventionally disposed in the housing 11, and also includes a motor shaft 27 rotatably mounted to the motor 26, and further includes a plurality of gears 28–31 one of which is conventionally mounted to the motor shaft 27 for rotation therewith, and also includes a cam shaft 32 being securely and conventionally disposed in the housing 11, and further includes a cam 34 being rotatably and conventionally mounted to the cam shaft 32 and being engageable to one of the gears 28–31, and also includes a plunger 37 being engageable to the cam 34 and to the nozzle 43 of the aerosol can 42, and further includes a power cord 41 being conventionally connected to the motor 26, and also includes a spring 40 being mounted about the plunger 37. The plunger 37 is movably extended through the first and second intermediate walls 24,25 and has a first end 38 which is engageable to the cam 34 and also has a second end 39 which is adapted to be engageable to the nozzle 43 of the aerosol can 42 with the plunger 37 being adapted to depress the nozzle 43 of the aerosol can 42 to effect dispensing of disinfectant spray from the aerosol can 42 through the nozzle 43 and through the first end 18 of the first tubular member 17. The spring 40 is disposed between the first and second intermediate walls 24,25 and is adapted to retain the plunger 37 in the housing 11 and through the first and second intermediate walls 24,25. The cam 34 is essentially oblong and has a first end portion 35 which is rotatably and conventionally mounted to the cam shaft 32 and also has a second end portion 36 which moves the plunger 37 toward the nozzle 43 of the aerosol can 42. The spray dispensing assembly also includes a gear shaft 33 being securely and conventionally disposed in the housing 11 with the gears 28–31 being mounted upon the motor shaft 28, the gear shaft 33 and the cam shaft 32.

In use, the user places a can of disinfectant spray in the housing 11 through the access opening 14 and upon a bottom wall 48 of the housing 11 with the nozzle 43 being in alignment with the first end 18 of the first tubular member 17 and being engageable to the second end 39 of the plunger 37. The user then connects the power cord 41 to a power supply which energizes the motor 26 which, in turn, rotates the motor shaft 27 which rotates and moves the gears 28–31 and the cam 34 which moves the plunger 37 toward the aerosol can 42 to depress the nozzle 43 which dispenses the spray from the aerosol can 42 through the conduit assembly into the heating and cooling duct 45. The spring 40 essentially moves the plunger 37 away from the nozzle 43 once the second end portion 36 of the cam 34 rotates beyond the first end 38 of the plunger 37.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A disinfectant distribution system for heating and cooling ducts comprising:

a housing structure assembly including a housing having a front wall, a back wall, side walls, and a top wall, and being adapted to be securely attached to a heating and cooling duct;

a conduit assembly being attached to and extended in said housing for transporting disinfectant spray from an aerosol can to the heating and cooling duct; and a spray dispensing assembly being disposed in said housing and being adapted to dispense disinfectant spray from the aerosol can;

wherein said conduit assembly includes a first tubular member having a first end extended in said housing through one of said side walls thereof and being adapted to be in alignment with a nozzle of the aerosol can, and also includes a tubular elbow member being mounted to a second end of said first tubular member, and further includes a second tubular member having a first end and a second end which is adapted to extend in the heating and cooling duct, said first end of said second tubular member being attached to said tubular elbow member.

2. A disinfectant distribution system for heating and cooling ducts as described in claim 1, wherein said housing structure assembly includes an access opening disposed through said front wall of said housing, and also includes a door removably closed over said access opening, and further includes flange members extending along bottom ends of said side walls and being adapted to securely mount said housing to the heating and cooling duct, said housing being adapted to receive and store the aerosol can therein.

3. A disinfectant distribution system for heating and cooling ducts as described in claim 1, wherein said housing structure also includes a first intermediate wall being disposed in said housing and being attached to said side walls thereof, and further includes a second intermediate wall being disposed below and spaced from said first intermediate wall in said housing.

4. A disinfectant distribution system for heating and cooling ducts as described in claim 1, wherein said spray dispensing assembly includes a motor securely disposed in said housing, and also includes a motor shaft rotatably mounted to said motor, and further includes a plurality of gears one of which is mounted to said motor shaft for rotation therewith, and also includes a cam shaft being securely disposed in said housing, and further includes a cam being rotatably mounted to said cam shaft and being engageable to one of said gears, and also includes a plunger being engageable to said cam and to a nozzle of the aerosol can, and further includes a power cord being connected to said motor, and also includes a spring mounted about said plunger for biasing said plunger away from the nozzle of the aerosol can.

5. A disinfectant distribution system for heating and cooling ducts as described in claim 4, wherein said housing structure also includes a first intermediate wall being disposed in said housing and being attached to said side walls thereof, and further includes a second intermediate wall being disposed below and spaced from said first intermediate wall in said housing, and wherein said plunger is movably extended through said first and second intermediate walls and has a first end which is engageable to said cam and also has a second end which is adapted to be engageable to the nozzle of the aerosol can, said plunger being adapted to depress the nozzle of the aerosol can to effect dispensing of disinfectant spray from the aerosol can through the nozzle and through said first end of said first tubular member.

6. A disinfectant distribution system for heating and cooling ducts as described in claim 4, wherein said housing structure also includes a first intermediate wall being disposed in said housing and being attached to said side walls thereof, and further includes a second intermediate wall being disposed below and spaced from said first intermediate wall in said housing, and wherein said spring is disposed between said first and second intermediate walls and is adapted to retain said plunger and to move the plunger away from the nozzle of the aerosol can.

7. A disinfectant distribution system for heating and cooling ducts as described in claim 4, wherein said cam is essentially oblong and has a first end portion which is rotatably mounted to said cam shaft and also has a second end portion which moves said plunger toward the nozzle of the aerosol can.

8. A disinfectant distribution system for heating and cooling ducts as described in claim 4, wherein said spray dispensing assembly also includes a gear shaft being securely disposed in said housing, said gears being mounted upon said motor shaft, said gear shaft and said cam shaft.

9. A disinfectant distribution system for heating and cooling ducts as described in claim 3, wherein said housing structure assembly also includes insulating material lining said side walls, said back wall, and said front wall in said housing between said second intermediate wall and said bottom wall of said housing.

10. A disinfectant distribution system for heating and cooling ducts comprising:

a housing structure assembly including a housing having a front wall, a back wall, side walls, and a top wall, and being adapted to be securely attached to a heating and cooling duct;

a conduit assembly being attached to and extended in said housing for transporting disinfectant spray from an aerosol can to the heating and cooling duct; and a spray dispensing assembly being disposed in said housing and being adapted to dispense disinfectant spray from the aerosol can;

wherein said housing structure assembly includes an access opening disposed through said front wall of said housing, and also includes a door removably closed over said access opening, and further includes flange members extending along bottom ends of said side walls and being adapted to securely mount said housing to the heating and cooling duct, said housing being adapted to receive and store the aerosol can therein;

wherein said housing structure also includes a first intermediate wall being disposed in said housing and being attached to said side walls thereof, and further includes a second intermediate wall being disposed below and spaced from said first intermediate wall in said housing;

wherein said conduit assembly includes a first tubular member having a first end extended in said housing through one of said side walls thereof and being adapted to be in alignment with a nozzle of the aerosol can, and also includes a tubular elbow member being mounted to a second end of said first tubular member, and further includes a second tubular member having a first end and a second end which is adapted to extend in the heating and cooling duct, said first end of said second tubular member being attached to said tubular elbow member.

11. A disinfectant distribution system for heating and cooling ducts as described in claim 10, wherein said spray dispensing assembly includes a motor securely disposed in said housing, and also includes a motor shaft rotatably mounted to said motor, and further includes a plurality of gears one of which is mounted to said motor shaft for rotation therewith, and also includes a cam shaft being disposed in said housing, and further includes a cam being rotatably mounted to said cam shaft and being engageable to one of said gears, and also includes a plunger being engageable to said cam and to a nozzle of the aerosol can, and further includes a power cord being connected to said motor, and also includes a spring mounted about said plunger for biasing said plunger away from the nozzle of the aerosol can.

12. A disinfectant distribution system for heating and cooling ducts as described in claim 11, wherein said plunger is movably extended through said first and second intermediate walls and has a first end which is engageable to said cam and also has a second end which is adapted to be engageable to the nozzle of the aerosol can, said plunger being adapted to depress the nozzle of the aerosol can to effect dispensing of disinfectant spray from the aerosol can through the nozzle and through said first end of said first tubular member.

13. A disinfectant distribution system for heating and cooling ducts as described in claim 11, wherein said spring is disposed between said first and second intermediate walls and is adapted to retain said plunger and to move the plunger away from the nozzle of the aerosol can.

14. A disinfectant distribution system for heating and cooling ducts as described in claim 11, wherein said cam is essentially oblong and has a first end portion which is rotatably mounted to said cam shaft and also has a second end portion which moves said plunger toward the nozzle of the aerosol can.

15. A disinfectant distribution system for heating and cooling ducts as described in claim 11, wherein said spray dispensing assembly also includes a gear shaft being securely disposed in said housing, said gears being mounted upon said motor shaft, said gear shaft and said cam shaft.

16. A disinfectant distribution system for heating and cooling ducts as described in claim 10, wherein said housing structure assembly also includes insulating material lining said side walls, said back wall, and said front wall in said housing between said second intermediate wall and said bottom wall of said housing.

17. A disinfectant distribution system for heating and cooling ducts comprising:

a housing structure assembly including a housing having a front wall, a back wall, side walls, and a top wall, and being adapted to be securely attached to a heating and cooling duct, said housing structure assembly including an access opening disposed through said front wall of said housing, and also including a door removably closed over said access opening, and further including flange members extending along bottom ends of said side walls and being adapted to securely mount said housing to the heating and cooling duct, said housing being adapted to receive and store the aerosol can therein, said housing structure also including a first intermediate wall being disposed in said housing and being attached to said side walls thereof, and further including a second intermediate wall being disposed below and spaced from said first intermediate wall in said housing, said housing structure assembly also including insulating material lining said side walls, said back wall, and said front wall in said housing between said second intermediate wall and said bottom wall of said housing;

a conduit assembly being attached to and extended in said housing for transporting disinfectant spray from an aerosol can to the heating and cooling duct, said conduit assembly including a first tubular member having a first end extended in said housing through one of said side walls thereof and being adapted to be in alignment with a nozzle of the aerosol can, and also including a tubular elbow member being mounted to a second end of said first tubular member, and further including a second tubular member having a first end and a second end which is adapted to extend in the heating and cooling duct, said first end of said second tubular member being attached to said tubular elbow member; and a spray dispensing assembly being disposed in said housing and being adapted to dispense disinfectant spray from the aerosol can, said spray dispensing assembly including a motor securely disposed in said housing, and also including a motor shaft rotatably mounted to said motor, and further including a plurality of gears one of which is mounted to said motor shaft for rotation therewith, and also including a cam shaft being securely disposed in said housing, and further including a cam being rotatably mounted to said cam shaft and being engageable to one of said gears, and also including a plunger being engageable to said cam and to a nozzle of the aerosol can, and further including a power cord being connected to said motor, and also including a spring mounted about said plunger, said plunger being movably extended through said first and second intermediate walls and having a first end which is engageable to said cam and also having a second end which is adapted to be engageable to the nozzle of the aerosol can, said plunger being adapted to depress the nozzle of the aerosol can to effect dispensing of disinfectant spray from the aerosol can through the nozzle and through said first end of said first tubular member, said spring being disposed between said first and second intermediate walls and being adapted to retain said plunger in said housing, said cam being essentially oblong and having a first end portion which is rotatably mounted to said cam shaft and also having a second end portion which moves said plunger toward the nozzle of the aerosol can, said spray dispensing assembly also including a gear shaft being securely disposed in said housing, said gears being mounted upon said motor shaft, said gear shaft and said cam shaft.

* * * * *